United States Patent [19]
Cohen

[11] Patent Number: 6,096,886
[45] Date of Patent: Aug. 1, 2000

[54] MORPHOLINO END-CAPPED, HINDERED AMINE SUBSTITUTED AMINOTRIAZINE

[75] Inventor: Martin L. Cohen, White Plains, N.Y.

[73] Assignee: Cytec Technology Corp., Wilmington, Del.

[21] Appl. No.: 09/184,885

[22] Filed: Nov. 3, 1998

Related U.S. Application Data

[60] Provisional application No. 60/067,730, Dec. 8, 1997.

[51] Int. Cl.⁷ .................................................. C07D 413/04
[52] U.S. Cl. ............................................ 544/112; 544/83
[58] Field of Search ........................................ 544/112, 83

[56] References Cited

U.S. PATENT DOCUMENTS

| | | |
|---|---|---|
| 4,086,204 | 4/1978 | Cassandrini et al. . |
| 4,104,248 | 8/1978 | Cantatore . |
| 4,325,863 | 4/1982 | Hinsken et al. . |
| 4,331,586 | 5/1982 | Hardy . |
| 4,338,244 | 7/1982 | Hinsken et al. . |
| 4,619,956 | 10/1986 | Susi . |
| 5,047,531 | 9/1991 | Cantatore et al. . |
| 5,106,891 | 4/1992 | Valet . |
| 5,130,429 | 7/1992 | Piccinelli et al. . |
| 5,175,312 | 12/1992 | Dubs et al. . |
| 5,216,052 | 6/1993 | Nesvadba et al. . |
| 5,252,643 | 10/1993 | Nesvadba . |
| 5,416,215 | 5/1995 | Buschken et al. . |

FOREIGN PATENT DOCUMENTS

| | | |
|---|---|---|
| 2167660 | 7/1996 | Canada . |
| 0 309 402 A1 | 3/1989 | European Pat. Off. . |
| 0 357 223 A3 | 3/1990 | European Pat. Off. . |
| 0 377 324 A3 | 7/1990 | European Pat. Off. . |
| 0 434 608 A1 | 6/1991 | European Pat. Off. . |
| 0 591 102 A1 | 9/1992 | European Pat. Off. . |
| 0 569 334 A1 | 11/1993 | European Pat. Off. . |
| 0 589 839 A1 | 3/1994 | European Pat. Off. . |
| 0 690 094 A1 | 6/1994 | European Pat. Off. . |
| 0 309 401 B1 | 10/1994 | European Pat. Off. . |
| 0 309 402 B1 | 1/1995 | European Pat. Off. . |
| 0 723 990 A1 | 1/1995 | European Pat. Off. . |
| 0 782 994 A1 | 7/1997 | European Pat. Off. . |
| 4316611 | 11/1993 | Germany . |
| 4316622 | 11/1993 | Germany . |
| 4316876 | 11/1993 | Germany . |
| 63-196654 | 8/1988 | Japan . |
| 2 269 819 | 2/1994 | United Kingdom . |

*Primary Examiner*—Robert W. Ramsuer
*Attorney, Agent, or Firm*—Michelle A. Sherwood; Claire M. Schultz; Michael J. Kelly

[57] ABSTRACT

Novel morpholino end-capped polyamino-1,3,5-triazines, methods for their use as light stabilizers for materials which are subject to degradation (for example, by actinic radiation), stabilizer compositions based on these morpholino end-capped polyamino-1,3,5-triazines and methods for their synthesis are herein described.

18 Claims, No Drawings

MORPHOLINO END-CAPPED, HINDERED AMINE SUBSTITUTED AMINOTRIAZINE

This application claims priority of co-pending U.S. Provisional Application Ser. No. 60/067.730 filed Dec. 8, 1997.

BACKGROUND OF THE INVENTION

1. Field of the Invention

This invention relates generally to novel morpholino end-capped, hindered amine substituted aminotriazines and the use thereof as a hindered amine light stabilizer.

2. Description of Related Art

It is well known that sunlight and other sources of ultraviolet light radiation cause degradation of polymers as evidenced by the embrittlement or yellowing of plastic articles made therefrom. It is also well known that this degradation can be inhibited by use of light stabilizers incorporated in or on such articles.

The reaction products of 2-substituted-4,6-dihalo-1,3,5-triazines and α,ω-diamines that have a 2,2,6,6-tetraalkyl-4-piperidinyl group on the nitrogen atoms thereof, are in general known as ultraviolet light stabilizers. It is believed that amino-1,3-5-triazines that bear such 2,2,6,6-tetraalkyl-4-piperidinyl groups function as free radical scavengers. Disclosures of a number of such "polyamino-1,3,5-triazines" can be found in the following publications, all of which are incorporated by reference herein for all purposes as if fully set forth: U.S. Pat. No. 4,086,204, U.S. Pat. No. 4,331,586, U.S. Pat. No. 5,021,485, U.S. Pat. No. 5,047,531, U.S. Pat. No. 5,130,429, U.S. Pat. No. 5,416,215, EP-A-0357223, EP-A-0309400, EP-A-0309401, EP-A-0309402, EP-A-0377324, EP-A-0569334, EP-A-0690094, EP-A-0723990, CA-A-2167660 and JP-A-63196654.

Typically, ultraviolet light stabilizers and in particular, polyamino-1,3,5-triazines, are blended or co-extruded with polymeric materials that are subject to exposure to various levels of ultraviolet radiation.

Certain known polyamino-1,3,5-triazines can exhibit high viscosity even at elevated temperatures. Due to their inherently high viscosity problems, these certain polyamino-1,3,5-triazines require high processing temperatures which can result in thermal degradation of the polyamino-1,3,5-triazine or polymer into which the polyamino-1,3,5-triazine is incorporated, as well as long term wear and tear on processing equipment, resulting in added maintenance and/or replacement costs. Accordingly, polyamino-1,3,5-triazines that have relatively lower processing temperatures, while at the same time are capable of functioning as effective free-radical scavengers, would be highly desirable.

SUMMARY OF THE INVENTION

The present invention provides a new class of polyamino-1,3,5-triazine ultraviolet light stabilizers which bear cyclohexylamino groups pendant from the triazine ring, and which are end-capped with a morpholino group. More specifically, the new polyamino-1,3,5-triazines of the present invention, useful as ultraviolet light stabilizing agents, have the following general formula (I):

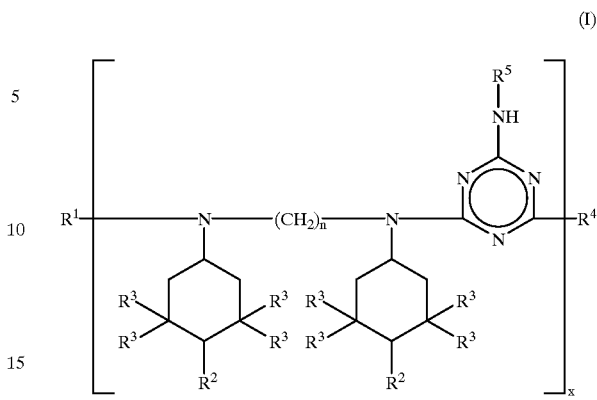

wherein $R^1$ is selected from hydrogen, hydrocarbyl, hydrocarbyloxy and a group of the formula (II)

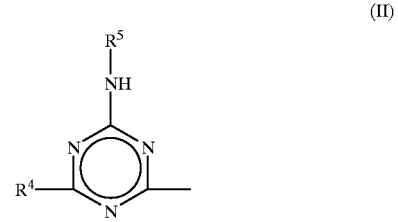

each $R^2$ is independently selected from hydrogen, oxyl, hydroxy, hydrocarbyl and hydrocarbyloxy;

each $R^3$ is independently selected from an alkyl of 1 to 5 carbon atoms;

each of $R^4$ and $R^5$ is independently a hydrocarbyl group;

n is 2–12; and x is 1–50, characterized in that each $R^4$ is a morpholino group, and each $R^5$ is a cyclohexyl group.

These polyamino-1,3,5-triazines may be prepared by reacting cyclohexylamine with a 2,4,6-trihalocyanurate, preferably, cyanuric chloride, and preferably in the presence of base, to afford a 2,6-dihalo-4-cyclohexylamino-1,3,5-triazine; the 2,6-dihalo-4-cyclohexylamino-1,3,5-triazine being reacted with an N,N'-bis(2,2,6,6-tetramethyl-4-piperidinyl)-α,ω-($C_2$–$C_{12}$)alkylenediamine, preferably in the presence of a base, to afford a polyamino-1,3,5-triazine; the polyamino-1,3,5-triazine being reacted with morpholine to afford the present cyclohexylamine substituted, morpholino end-capped polyamino-1,3,5-triazines. Further preferred process details are disclosed below.

The new polyamino-1,3,5-triazines of the present invention are particularly useful as ultraviolet light stabilizing agents for use in stabilizing a wide variety of organic substrates such as generally disclosed in the previously incorporated references including, for example, thermoplastic and crosslinked polymers such as polyesters, polyethers, polyurethanes, polystyrenes, high-impact polystyrenes, and preferably, polyolefins, used particularly as films, monofiliments, multifiliment yarns, coating matrices, and the like. The present invention, consequently, also relates to a method for stabilizing an organic material, e.g., a thermoplastic substrate, by incorporating into such organic material the inventive polyamino-1,3,5-triazines in an amount effective to stabilize the organic material against the effects of actinic radiation, and the organic material so stabilized.

These and other features and advantages of the present invention will be more readily understood by those of ordinary skill in the art from a reading of the following detailed description.

DETAILED DESCRIPTION OF THE PREFERRED EMBODIMENTS

The Novel Polyamino-1,3,5-Triazines

As indicated above, the polyamino-1,3,5-triazines in accordance with the present invention are compounds of the above general formula (I).

The term "hydrocarbyl" in the context of the present invention, and in the above formulas, broadly refers to a monovalent hydrocarbon group in which the valency is derived by abstraction of a hydrogen from a carbon atom. Hydrocarbyl includes, for example, aliphatics (straight and branched chain), cycloaliphatics, aromatics and mixed character groups (e.g., aralkyl and alkaryl). Hydrocarbyl also includes such groups with internal unsaturation and activated unsaturation. More specifically, hydrocarbyl includes (but is not limited to) such groups as alkyl, cycloalkyl, aryl, aralkyl, alkaryl, alkenyl, cycloalkenyl and alkynyl, preferably having up to 24 carbon atoms. A hydrocarbyl may optionally contain a carbonyl group or groups (which is/are included in the carbon count) and/or a heteroatom or heteroatoms (such as at least one oxygen, sulfur, nitrogen or silicon), in the chain or ring.

The term "hydrocarbyloxy" in the context of the present invention means hydrocarbyl-O—. The term "hydrocarboyl" as used herein means hydrocarbyl-co-.

In preferred embodiments, $R^1$ is hydrogen or group (II) depicted above and, more preferably group (II).

In preferred embodiments, each $R^2$ is independently selected hydrogen, hydrocarbyl and hydrocarbyloxy and, more preferably, from hydrogen, an alkyl of 1 to 4 carbon atoms, and alkoxy of 1 to 4 carbon atoms, and an acetyl group.

In preferred embodiments, each $R^3$ is methyl.

In preferred embodiments, n is 4–8 and especially 6, and x is 1–20 and especially 1–15.

Finally, further preferred embodiments may include any combination of parameters mentioned above.

Methods of Preparation

In general, the polyamino-1,3,5-triazines of the present invention can be prepared by the methods generally described in the previously incorporated references.

In a preferred process, a 2,6-dihalo-4-cyclohexylamino-1,3,5-triazine is reacted with an N,N'-bis(2,2,6,6-tetraalkyl-4-piperidinyl)-α,ω-($C_2$–$C_{12}$)alkylenediamine having the following formulas:

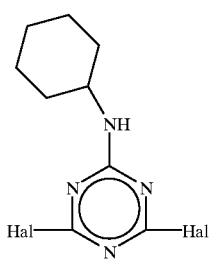

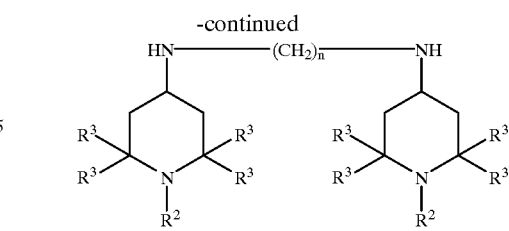

wherein Hal is a halogen preferably selected from Cl, Br and I, and especially Cl; and $R^2$ and $R^3$ are as defined above, under conditions to prepare a monomeric/oligomeric/polymeric intermediate terminated by Hal and/or hydrogens, then reacting (end-capping) this intermediate with morpholine to prepare the polyamino-1,3,5-triazine of the present invention.

The 2,6-dihalo-4-cyclohexylamino-1,3,5-triazine depicted above is typically obtained by reacting a 2,4,6-trihalocyanurate with cyclohexylamine in an amount sufficient to provide a 2,6-dihalo-4-cyclohexylamino-1,3,5-triazine with less than 25% combined yield of di- and tri-substituted side products. Such 2,4,6-trihalocyanurates can be obtained commercially, or by methods known to those skilled in the art. Preferably, the molar ratio of cyclohexylamine to the 2,4,6-trihalocyanurate is about 0.89:1 to about 1.10:1, more preferably about 0.95:1 to about 1.05:1, and most preferably about 1.01:1. In a preferred embodiment, the 2,4,6-trihalocyanurate is cyanuric chloride.

The reaction between the 2,4,6-trihalocyanurate and cyclohexylamine can occur in monophasic solution in an organic solvent including, but not limited to, methylene chloride, chloroform, carbon tetrachloride, tetrahydrofuran, diethyl ether, ethyl acetate, benzene, toluene, xylenes, and the like, preferably in the presence of an organic and/or inorganic base. As suitable organic bases may be mentioned organic amines such as pyridine, 4-dimethylaminopyridine, triethylamine, ethyl diisopropylamine, 1,8-diazabicyclo(5.4.0)undec-7-ene, 1,5-diazabicyclo(4.3.0)non-5-ene, 1,4-diazabicyclo(2.2.2)octane, N,N,N',N'-1,8-bis(dimethylamino)naphthalene and the like, and mixtures thereof. As suitable inorganic bases may be mentioned alkali metal hydroxides, alkali metal carbonates or bicarbonates, and alkaline earth carbonates, as well as mixtures thereof. Mixtures of organic and inorganic bases may also be utilized.

Preferably, however, the reaction between the 2,4,6-trihalocyanurate and cyclohexylamine occurs in a biphasic mixture of an organic solvent and water, the organic solvent being methylene chloride, chloroform, carbon tetrachloride, benzene, toluene, xylenes, or the like, and further in the presence of an organic and/or a inorganic base, such as those mentioned above.

In either the monophasic or biphasic system, the preferred base is an inorganic base and especially sodium hydroxide, which is preferably utilized in a molar ratio of base to the 2,4,6-trihalocyanurate is about 0.92:1 to about 1.15:1, and more preferably about 0.99:1 to about 1.08:1, and especially at a slight molar excess (such as 1.01:1). Molar ratios for other bases would typically be similar to sodium hydroxide, adjusted for the number of base equivalents per mole.

In the biphasic system, an inorganic base can conveniently be employed as an aqueous solution, preferably at about 10% to about 60%, more preferably at about 40% to about 60%, and most preferably at about 50%, weight/ weight. In a preferred embodiment, the reaction between the 2,4,6-trihalocyanurate and cyclohexylamine occurs in a biphasic mixture of toluene and water, and in the presence of sodium hydroxide. In this preferred embodiment, the sodium hydroxide is employed as a 50% (weight/weight) aqueous solution.

Generally, the ratio (w/w) of organic solvent to the 2,4,6-trihalocyanurate is about 1:1 to about 10:1, preferably about 2.3:1 to about 3:1. Where the reaction between the 2,4,6-trihalocyanurate and cyclohexylamine occurs in a biphasic mixture of an organic solvent and water, the ratio (w/w) of the organic solvent to the overall water content is about 3:1 to about 1.5:1, preferably about 2.0:1 to about 1.5:1.

Typically, the cyclohexylamine is added to a mixture of the 2,4,6-trihalocyanurate and the organic solvent, and at a rate such that the reaction temperature remains at between about −5° C. to about 15° C., preferably at between about 0° C. to about 10° C. To the resulting mixture is then added the base, preferably sodium hydroxide, at a rate such that the reaction temperature remains at between about −5° C. to about 15° C., preferably at between about 0° C. to about 10° C., affording a predominant amount of the desired 2,6-dihalo-4-cyclohexylamino-1,3,5-triazine intermediate. As indicated above, the preferred 2,4,6-trihalocyanurate is cyanuric chloride, meaning that the resulting desired 2,6-dihalo-4-cyclohexylamino-1,3,5-triazine is 2,6-dichloro-4-cyclohexylamino-1,3,5-triazine.

It is to be pointed out that along with the 2,6-dihalo-4-cyclohexylamino-1,3,5-triazine, small amounts of 2-halo-4,6-bis(cyclohexylamino)-1,3,5-triazine and 2,4,6-tris(cyclohexylamino)-1,3,5-triazine side products may also be formed. If desired, such side products can be removed via known techniques such as selective recrystallization.

The 2,6-dihalo-4-cyclohexylamino-1,3,5-triazine intermediate is then admixed, at a temperature of about 50° C. to about 100° C., preferably at about 700° C. to about 800° C., with the N,N'-bis(2,2,6,6-tetramethyl-4-piperidinyl)-α,ω-($C_2$–$C_{12}$)alkylenediamine depicted above, to provide the polyamino-1,3,5-triazine in accordance with the present invention. The N,N'-bis(2,2,6,6-tetramethyl-4-piperidinyl)-α,ω-($C_2$–$C_{12}$)alkylenediamine can be obtained by means well-known to those of ordinary skill in the art, such as disclosed in Example 2 of previously incorporated U.S. Pat. No. 4,104,248. Preferably, such is obtained by reacting about 2 eq. of 2,2,6,6-tetramethyl-4-piperidone with about 1 eq. of an α,ω-($C_2$–$C_{12}$)alkylenediamine to afford a corresponding bis(imine), and reducing the bis(imine) with, for example, $H_2$ in the presence of $PtO_2$, to afford the N,N'-bis(2,2,6,6-tetramethyl-4-piperidinyl)-α,ω-($C_2$–$C_{12}$)alkylenediamine.

If it is desired that the N,N'-bis(2,2,6,6-tetramethyl-4-piperidinyl)-α,ω-($C_2$–$C_{12}$)alkylenediamine be substituted at one or both of piperidyl nitrogen atoms, it can be modified, for example, by methylation according to the procedures detailed in previously incorporated U.S. Pat. No. 5,130,429 (see Example 1, part b); by alkoxylation according to the procedures detailed in previously incorporated EP-A-0569334 (see Example 1); and by oxylation according to the procedures detailed in previously incorporated U.S. Pat. No. 5,416,215 (see Example 2).

The reaction between the 2,6-dihalo-4-cyclohexylamino-1,3,5-triazine and the N,N'-bis(2,2,6,6-tetramethyl-4-piperidinyl)-α,ω-($C_2$–$C_{12}$)alkylenediamine advantageously proceeds in the presence of a base, such as the inorganic and/or organic bases described above. Preferred is an inorganic base, particularly an alkali metal carbonate, and especially sodium carbonate.

The inorganic bases can be solvated with the aid of water. In such a case, the ratio (w/w) of water to the 2,4,6-trihalocyanurate (used in preparing the 2,6-dihalo-4-cyclohexylamino-1,3,5-triazine intermediate) is in the range of from about 1.05:1 to about 1.10:1.

The molar ratio of N,N'-bis(2,2,6,6-tetramethyl-4-piperidinyl)-α,ω-($C_2$–$C_{12}$)alkylenediamine to the 2,4,6-trihalocyanurate (used in preparing the 2,6-dihalo-4-cyclohexylamino-1,3,5-triazine intermediate) is preferably in the range of from about 0.5:1 to about 1.5:1, and more preferably from about 0.8:1 to about 1.2:1. The molar ratio of the preferred inorganic base (sodium carbonate, to the 2,4,6-trihalocyanurate (used in preparing the 2,6-dihalo-4-cyclohexylamino-1,3,5-triazine intermediate) is about 0.8:1 to about 1.2:1, preferably about 1:1. Molar ratios for other bases can be readily determined by adjusting for the number of base equivalents per mole.

The mixture containing the 2,6-dihalo-4-cyclohexylamino-1,3,5-triazine intermediate, the N,N'-bis(2,2,6,6-tetramethyl-4-piperidinyl)-α,ω-($C_2$–$C_{12}$)alkylenediamine and the base is heated at a temperature of from about 50° C. to about the reflux temperature of the organic solvent(s) used in the process. Preferably, a biphasic mixture of toluene and water, such as used in the initial reaction between the 2,4,6-trihalocyanurate and cyclohexylamine, and the above mixture is heated at a temperature and for a time so as to form a monomeric/oligomeric/polymeric mixture of products containing 1–30, and preferably 1–20, repeat units while removing water and toluene by distillation as a water/toluene azeotrope. Depending on solvent choice, this reaction temperature will typically be in the range of from about 90° C. to about 105° C., preferably at about 98° C. to about 102° C. Once the water/toluene azeotrope begins to distill from the reaction mixture, the reaction mixture is heated for about 30 minutes to about 48 hours, preferably for about 4 to about 24 hours.

To this reaction mixture is then added morpholine, so as to end cap the product to ultimately form the polyamino-1,3,5-triazines of the present invention (wherein the $R^4$ groups are morpholino). The molar ratio of morpholine to the 2,4,6-trihalocyanurate (used in the preparation of the 2,6-dihalo-4-cyclohexylamino-1,3,5-triazine intermediate) is typically about 0.10:1 to about 1.5:1, and preferably about 0.5:1 to about 0.7:1.

Optionally, and preferably, the morpholine may be added to the reaction mixture in conjunction with an organic solvent such as one described above, or a mixture of organic solvents. If it is desired that an organic solvent is added in conjunction with the morpholine, the ratio (w/w) of organic solvent to the 2,4,6-trihalocyanurate (used in the preparation of the 2,6-dihalo-4-cyclohexylamino-1,3,5-triazine intermediate) is about 1:1 to about 1.5:1.

Following the addition of morpholine, and optionally the organic solvent, the reaction mixture is heated, preferably at the reflux temperature of the reaction mixture, typically for about 15 minutes to about 6 hours, and preferably for about 30 minutes to about 2 hours, so as to facilitate morpholine end-capping and achieve the desired end product.

Advantageously, the resulting product is treated with a base, such as an organic and/or inorganic base described above, and preferably sodium hydroxide. The addition of such a base acts as a scavenger for any residual hydrogen halide by-product from the reaction between the 2,4,6-trihalocyanurate and the N,N'-bis(2,2,6,6-tetramethyl-4-piperidinyl)-α,ω-($C_2$–$C_{12}$)alkylenediamine, as well as ensure that the polyamino-1,3,5-triazine exists in its free-base form. When employed, this additional base is conveniently an aqueous solution, preferably at a concentration of from about 10% to about 60%, more preferably at about 40% to about 60%, weight/weight, and is added in a molar ratio, for the preferred base sodium hydroxide, relative to the amount of 2,4,6-trihalocyanurate originally used in the reaction, of about 0.3:1 to about 0.5:1.

Following addition of the base, the reaction mixture can be heated, preferably at its reflux temperature, typically for about 15 minutes to about 6 hours, and preferably for about 30 minutes to about 2 hours.

If an aqueous base is used in any of the above steps, the resulting reaction mixture will be biphasic, with the polyamino-1,3,5-triazine residing in the organic phase. To recover the polyamino-1,3,5-triazine, the aqueous phase is removed and discarded, and the remaining organic phase is concentrated, preferably in vacuo, to provide the polyamino-1,3,5-triazine of the present invention. If desired, the resulting product can be further purified by solvent/non-solvent precipitation techniques well known to those skilled in the art.

Stabilizer Composition

From the above process discussion, it is evident that the resulting polyamino-1,3,5-triazine product will actually be a mixture of various monomeric, oligomeric and/or polymeric species, for example, where $R^1$ is predominantly hydrogen or the substituted triazine group, and x is preferably in the range of from 1 to 30. These stabilizer composition products, comprising a mixture of compounds of the formula (I), also form a part of the present invention.

Preferably, such mixtures possess a number average molecular weight ($M_n$) of from about 1200 to about 3000, and more preferably from about 1500 to about 2500, and a weight average molecular weight ($M_w$) of from about 2000 to about 5500, and more preferably from about 2400 to about 4500, as measured by high performance size exclusion chromatography (HPSEC).

Uses of the Polyamino-1,3,5-Triazines

The polyamino-1,3,5-triazines and stabilizer compositions of the present invention are particularly useful as an ultraviolet light stabilizer additive for stabilizing a wide variety of organic materials, in particular, those subject to degradation by actinic radiation. Such organic materials include, for example, various organic polymers (both crosslinked and thermoplastic) including polyolefins, polyesters, polyethers, polyurethanes, polystyrenes and high-impact polystyrenes; photographic materials and dye solutions for textile materials; as well as in ultraviolet light screening agents (such as sunscreens), as disclosed below. The polyamine-1,3,5-triazines can be incorporated into such material in any one of a variety of conventional manners such as disclosed in the previously incorporated references including, for example, physical mixing or blending.

Examples of materials into which the polyamine-1,3,5-triazines of the present invention can be incorporated and accordingly, stabilized, include, for example:

1. Homo- and copolymers of monoolefins and diolefins including but not limited to ethylene, propylene, isobutylene, butene, methylpentene, hexene, heptene, octene, isoprene, butadiene, hexadiene, dicyclopentadiene, ethylidene and cycloolefins such as cyclopentene and norbornene; for example, polyethylenes (which optionally can be crosslinked) such as high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE) and branched low density polyethylene (BLDPE).

2. Copolymers of one or more monoolefins and/or diolefins with carbon monoxide and/or with other vinyl monomers, including limited acrylic and methacrylic acid, acrylates and methacrylates, acrylamides, acrylonitriles, styrenes, vinyl acetate (such as ethylene/vinyl acetate copolymers), vinyl halides, vinylidene halides, maleic anhydride and allyl monomers such as allyl alcohol, allyl amine ally glycidyl ether and derivatives thereof.

3. Hydrocarbon resins (such as $C_5$–$C_9$) including hydrogenated modifications thereof and mixtures of polyalkylenes and starch.

4. Homo- and copolymers of styrenes such as styrene, p-methylstyrene and α-methylstyrene.

5. Copolymers of one or more styrenes with other vinyl monomers such as olefins and diolefins (e.g., ethylene, isoprene and/or butadiene), acrylic and methacrylic acid, acrylates and methacrylates, acrylamides, acrylonitriles, vinyl acetate (such as ethylene/vinyl acetate copolymers), vinyl halides, vinylidene halides, maleic anhydride and allyl compounds such as allyl alcohol, allyl amine allyl glycidyl ether and derivatives thereof.

6. Graft copolymers of styrenes on polybutadienes, polybutadiene/styrene copolymers and polybutadiene/acrylonitrile copolymers; styrene (or α-methylstyrene) and acrylonitrile (or methacrylonitrile) on polybutadiene; styrene and maleic anhydride on polybutadiene; styrene, acrylonitrile and maleic anhydride or maleimide on polybutadiene; styrene and acrylonitrile on ethylene/propylene/diene copolymers; styrene and acrylonitrile on polyalkyl acrylates or methacrylates; and styrene and acrylonitrile on acrylate/butadiene copolymers.

7. Halogen-containing polymers such as polychloroprene; chlorinated rubbers; chlorinated and brominated isobutylene/isoprene copolymers; chlorinated or sulfochlorinated polyethylene; copolymers of ethylene and chlorinated ethylene; epichlorohydrin polymers and copolymers; and polymers and copolymers of halogen-containing vinyl compounds such as vinyl chloride, vinylidene chloride, vinyl fluoride and/or vinylidene fluoride and other vinyl monomers.

8. Homo- and copolymers derived from α,β-unsaturated acids and derivatives thereof such as acrylic acid, methacrylic acid, acrylates, methacrylates, acrylamides and acrylonitriles.

9. Copolymers of the monomers mentioned in (8) with other unsaturated monomers such as olefins and diolefins (e.g., butadiene), styrenes, vinyl halides, maleic anhydride and allyl monomer such as allyl alcohol, allyl amine, allyl glycidyl ether and derivatives thereof.

10. Homo- and copolymers derived from unsaturated alcohols and amines or the acyl derivatives or acetals thereof, such as vinyl alcohol, vinyl acetate, vinyl stearate, vinyl benzoate, vinyl maleate, vinyl butyral, allyl alcohol, allyl amine, allyl glycidyl ether, allyl phthalate and allyl melamine; as well as copolymers of such monomers with other ethylenically unsaturated monomers mentioned above.

11. Homo- and copolymers of cyclic ethers such as alkylene glycols and alkylene oxides, as well as copolymers with bisglycidyl ethers.

12. Polyacetals such as polyoxymethylene and those polyoxymethylenes which contain ethylene oxide as a comonomer; and polyoxymethylenes modified with thermoplastic polyurethanes, acrylates and/or MBS.

13. Polyphenylene oxides and sulfides.

14. Polyurethanes derived from hydroxy-functional components such as polyhydric alcohols, polyethers, polyesters, polyacrylics and/or polybutadienes on the one hand, and aliphatic and/or aromatic isocyanates on the other, as well as precursors thereof.

15. Polyamides and copolyamides derived from diamines, dicarboxylic acids and/or aminocarboxylic acids or the corresponding lactams, such as polyamide 4, polyamide 6, polyamide 6/6, polyamide 6/10, polyamide 6/9, polyamide 6/12, polyamide 4/6, polyamide 12/12, polyamide 11 and polyamide 12; aromatic polyamides starting from m-xylene diamine and adipic acid; polyamides prepared from hexamethylene diamine and isophthalic and/or terephthalic acid and with or without an elastomer as a modifier, for example, poly-2,4,4-trimethylhexamethylene terephthalamide or poly-m-phenylene isophthalamide; block copolymers of the aforementioned polyamides with polyolefins, olefin copolymer, ionomers, chemically bonded or grafted elastomers, or polyethers such as polyethylene glycol, polypropylene glycol or polytetramethylene glycol; and polyamides condensed during processing (RIM polyamide systems).

16. Polyureas, polyimides, polyamide-imides, polyetherimides, polyesterimides, polyhydantoins and polybenzimidazoles.

17. Polyesters derived from dicarboxylic acids, diols and/or hydroxycarboxylic acids or the corresponding lactones, such as polyethylene terephthalate, polybutylene terephthalate, poly-1,4-dimethylcyclohexane terephthalate and polyhydroxybenzoates, as well as block copolyether esters derived from hydroxyl-terminated ethers; and also polyesters modified with polycarbonate or MBS.

18. Polycarbonates and polyester carbonates.

19. Polysulfones, polyether sulfones and polyether ketones.

20. Crosslinked polymers derived from aldehydes condensation resins such as phenol/formaldehyde resins, urea/formaldehyde resins and melamine/formaldehyde resins.

21. Drying and non-drying alkyd resins.

22. Unsaturated polyester resins derived from copolyesters of saturated and unsaturated dicarboxylic acids with polyhydric alcohols and vinyl compounds as crosslinking agents and also halogen-containing modifications thereof.

23. Crosslinkable acrylic resins derived from substituted acrylates such as epoxy acrylates, hydroxy acrylates, isocyanato acrylates, urethane acrylates or polyester acrylates.

24. Alkyd resins, polyester resins and acrylate resins crosslinked with melamine resins, urea resins, isocyanates, isocyanurates, carbamates or epoxy resins.

25. Crosslinked epoxy resins derived from aliphatic, cycloaliphatic, heterocyclic and/or aromatic glycidyl compounds such as bisphenol A and bisphenol F, which are crosslinked with customary hardeners such as anhydrides or amines.

26. Natural polymers such as cellulose, rubber, gelatin and chemically modified homologous derivatives thereof, including cellulose acetates, cellulose propionates and cellulose butyrates, or the cellulose ethers such as methyl cellulose, as well as rosins and their derivatives.

27. Polysiloxanes.

28. Michael addition polymers of amines or blocked amines (e.g., ketimines) with activated unsaturated and/or methylene compounds such as acrylates and methacrylates, maleates and acetoacetates.

29. Mixtures or blends of any of the above, such as PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylate, POM/thermoplastic PUR, PC/thermoplastic polyurethane, POM/acrylate, POM/MBS, PPO/HIPS, PPO/PA6.6 and copolymers, PA/HDPE, PP/HDPE, PP/LDPE, LDPE/HDPE, LDPE/EVA, LDPE/EAA, PA/PP, PA/PPO, PBT/PC/ABS, PBT/PET/PC and the like.

30. Polyketimines in combination with unsaturated acrylic polyacetoacetate resins or with unsaturated acrylic resins including urethane acrylates, polyether acrylates, vinyl or acryl copolymers with pendant unsaturated groups and acrylated melamines.

31. Radiation curable compositions containing ethylenically unsaturated monomers or oligomers and a polyunsaturated aliphatic oligomer.

32. Epoxymelamine resins such as light-stable epoxy resins cross-linked by an epoxy functional coetherified high solids melamine resin. Other materials which can be stabilized include, for example:

33. Naturally occurring and synthetic organic materials which may be mixtures of compounds, including mineral oils, animal and vegetable fats, oils and waxes, or oils, fats or waxes based on synthetic esters (e.g., phthalates, adipates, phosphates or trimellitates) and also mixtures of synthetic esters with mineral oils in any ratio.

34. Aqueous emulsions of natural or synthetic rubber such as natural latex or lattices of carboxylated styrene/butadiene copolymers.

35. Organic dyes such as azo dyes (diazo, triazo and polyazo), anthraquinones, benzodifuranones, polycyclic aromatic carbonyl dyes, indigoid dyes, polymethines, styryl dyes, di- and triaryl carbonium dyes, phthalocyanines, quinophthalones, sulfur dyes, nitro and nitroso dyes, stilbene dyes, formazan dyes, quinacridones, carbazoles and perylene tetracarboxylic diimides.

36. Cosmetic products, such as skin lotions, collagen creams, sunscreen, facial make-up, etc., comprising synthetic materials such as antioxidants, preservatives, lipids, solvents, surfactants, colorants, antiperspirants, skin conditioners, moisturizers etc.; as well as natural products such as collagen, proteins, mink oil, olive oil, coconut oil, carnauba wax, beeswax, lanolin, cocoa butter, xanthan gum, aloe, etc.

37. Cellulose-based paper formulations for use, e.g., in newsprint, cardboard, posters, packaging, labels, stationery, book and magazine paper, bond typing paper, multi-purpose and office paper, computer paper, xerographic paper, laser and ink-jet printer paper, offset paper, currency paper, etc.

38. Photographic film paper.

39. Ink.

The polyamino-1,3,5-triazines of the present invention may be used in widely varying amounts in such applications depending upon such things as the material to be stabilized and the particular application. However, when employed as a stabilizing additive for materials such as organic polymers, the polyamino-1,3,5-triazines of the present invention are typically employed in amounts from about 0.01 to about 20% by weight, preferably from about 0.1 to about 10% by weight, and most preferably from about 0.1 to about 5% by weight, based on the weight of the material to be stabilized.

As examples of preferred polymers may be mentioned thermoplastic polymers such as polyolefins and/or polymers comprising heteroatoms in the main chain. Preferred polymers are also thermoplastic polymers comprising nitrogen, oxygen and/or sulphur, especially nitrogen or oxygen, in the main chain. Also of interest are compositions in which the polymer is a polyolefin, for example polyethylene or polypropylene.

Incorporation into the thermoplastic polymers can be carried out by addition of the polyamino-1,3,5-triazine compounds and any further additives by the methods conventional in the art. The incorporation can expediently be made before or during shaping, for example by mixing the pulyerulent components or by adding the stabilizer to the melt or solution of the polymer, or by applying the dissolved or dispersed compounds to the polymer, with or without subsequent evaporation of the solvent. Elastomers can also be stabilized as lattices.

The polyamino-1,3,5-triazines can also be added to the polymers to be stabilized in the form of a masterbatch which comprises these compounds, for example, in a concentration of from about 2.5 to about 25%, preferably from about 5 to about 20% by weight of the polymer.

These polyamino-1,3,5-triazines can expediently be incorporated into the polymeric material by any number of methods, including those conventionally employed in the art, including by, for example: a) as an emulsion or dispersion (for example to lattices or emulsion polymers); (b) as a dry mix during mixing of additional components or polymer mixtures; (c) by direct addition to the processing equipment (for example extruders, internal mixers, etc.); or (d) as a solution or melt.

The stabilized polymer compositions obtained in this way can be converted into shaped articles, for example fibers, films, tapes, sheets, sandwich boards, containers, pipes and other profiles, by any number of conventional methods, for example hot pressing, spinning, extrusion, roto-molding or injection molding. Therefore, the present invention additionally relates to the use of the polymer composition according to the invention for the production of a shaped article.

Depending upon their ultimate end use, the polyaminol-1,3,5-triazines of the present invention may be combined with a variety of additives conventionally employed in the stabilizing art. Examples of such additives include but are not limited to:

a. Antioxidants (i) Alkylated monophenols such as 2,6-di-tert-butyl-4-methylphenol; 2-tert-butyl-4,6-dimethylphenol; 2,6-di-tert-butyl-4-ethylphenol; 2,6-di-tert-butyl-4-n-butylphenol; 2,6-di-tert-butyl-4-isobutylphenol; 2,6-dicyclopentyl-4-methylphenol; 2-(α-methylcyclohexyl)-4,6-dimethylphenol; 2,6-dioctadecyl-4-methylphenol; 2,4,6-tricyclohexylphenol; 2,6-di-tert-butyl-4-methoxymethylphenol; nonylphenols which are linear or branched in the side chains such as 2,6-di-nonyl-4-methylphenol; 2,4-dimethyl-6-(1-methylundec-1-yl)phenol; 2,4-dimethyl-6-(1-methylheptadec-1-yl)phenol; 2,4-dimethyl-6-(1-methyltridec-1-yl)phenol; and mixtures thereof.

(ii) Alkylthiomethylphenols such as 2,4-dioctylthiomethyl-6-tert-butylphenol; 2,4-dioctylthiomethyl-6-methylphenol; 2,4-dioctylthiomethyl-6-ethylphenol; and 2,6-di-dodecylthiomethyl-4-nonylphenol.

(iii) Hydroquinones and alkylated hydroquinones such as 2,6-di-tert-butyl-4-methoxyphenol; 2,5-di-tert-butylhydroquinone; 2,5-di-tert-amylhydroquinone; 2,6-diphenyl-4-octadecyloxyphenol; 2,6-di-tert-butylhydroquinone; 2,5-di-tert-butyl-4-hydroxyanisole; 3,5-di-tert-butyl-4-hydroxyanisole; 3,5-di-tert-butyl-4-hydroxyphenyl stearate; and bis(3,5-di-tert-butyl-4-hydroxyphenyl)adipate.

(iv) Tocopherols such as α-tocopherol, β-tocopherol, γ-tocopherol, δ-tocopherol and mixtures thereof (vitamin E).

(v) Hydroxylated thiodiphenyl ethers such as 2,2'-thiobis(6-tert-butyl-4-methylphenol); 2,2'-thiobis(4-octylphenol); 4,4'-thiobis(6-tert-butyl-3-methylphenol); 4,4'-thiobis(6-tert-butyl-2-methylphenol); 4,4'-thiobis(3,6-di-sec-amylphenol); and 4,4'-bis(2,6-dimethyl-4-hydroxyphenyl)disulfide.

(vi) Alkylidenebisphenols such as 2,2'-methylenebis(6-tert-butyl-4-methylphenol); 2,2'-methylenebis(6-tert-butyl-4-ethylphenol); 2,2'-methylenebis[4-methyl-6-(α-methylcyclohexyl)phenol]; 2,2'-methylenebis(4-methyl-6-cyclohexylphenol); 2,2'-methylenebis(6-nonyl-4-methylphenol); 2,2'-methylenebis(4,6-di-tert-butylphenol); 2,2'-ethylidenebis(4,6-di-tert-butylphenol); 2,2'-ethylidenebis(6-tert-butyl-4-isobutylphenol); 2,2'-methylenebis[6-(α-methylbenzyl)-4-nonylphenol]; 2,2'-methylenebis[6-(α,α-dimethylbenzyl)-4-nonylphenol]; 4,4'-methylenebis(2,6-di-tert-butylphenol); 4,4'-methylenebis(6-tert-butyl-2-methylphenol); 1,1-bis(5-tert-butyl-4-hydroxy-2-methylphenyl)butane; 2,6-bis(3-tert-butyl-5-methyl-2-hydroxylbenzyl)-4-methylphenol; 1,1,3-tris(5-tert-butyl-4-hydroxy-2-methylphenyl)bu3333tane; 1,1-bis(5-tert-butyl-4-hydroxy-2-methylphenyl)-3-n-dodecylmercaptobutane; ethylene glycol bis[3,3-bis(3'-tert-butyl-4'-hydroxyphenyl)butyrate], bis(3-tert-butyl-4-hydroxy-5-methylphenyl)dicyclopentadiene; bis[2-(3'-tert-butyl-2'-hydroxy-5'-methylbenzyl)-6-tert-butyl-4-methylphenyl]terephthalate; 1,1-bis(3,5-dimethyl-2-hydroxyphenyl)butane; 2,2-bis(3,5-di-tert-butyl-4-hydroxyphenyl)propane; 2,2-bis(5-tert-butyl-4-hydroxy-2-methylphenyl)-4-n-dodecylmercaptobutane; and 1,1,5,5-tetra(5-tert-butyl-4-hydroxy-2-methylphenyl)pentane.

(vii) O-, N- and S-benzyl compounds such as 3,5,3',5'-tetra-tert-butyl-4,4'-dihydroxydibenzyl ether; octadecyl-4-hydroxy-3,5-dimethylbenzylmercaptoacetate; tridecyl-4-hydroxy-3,5-di-tert-butylbenzylmercaptoacetate; tris(3,5-di-tert-butyl-4-hydroxybenzyl)amine; bis(4-tert-butyl-3-hydroxy-2,6-dimethylbenzyl)dithioterephthalate; bis(3,5-di-tert-butyl-4-hydroxybenzyl)sulfide; and isooctyl-3,5-di-tert-butyl-4-hydroxybenzylmercaptoacetate.

(viii) Hydroxybenzylate malonates such as dioctadecyl-2,2-bis(3,5-di-tert-butyl-2-hydroxybenzyl)malonate; dioctadecyl-2-(3-tert-butyl-4-hydroxy-5-methylbenzyl)malonate; didodecylmercaptoethyl-2,2-bis(3,5-di-tert-butyl-4-hydroxybenzyl)malonate; and bis[4-(1,1,3,3-tetramethylbutyl)phenyl]-2,2-bis(3,5-di-tert-butyl-4-hydroxybenzyl)malonate.

(ix) Aromatic hydroxybenzyl compounds such as 1,3,5-tris(3,5-di-tert-butyl-4-hydroxybenzyl)-2,4,6-trimethylbenzene; 1,4-bis(3,5-di-tert-butyl-4-hydroxybenzyl)-2,3,5,6-tetramethylbenzene; and 2,4,6-tris(3,5-di-tert-butyl-4-hydroxybenzyl)phenol.

(x) Triazine compounds such as 2,4-bis(octylmercapto-6-(3,5-di-tert-butyl-4-hydroxyanilino)-1,3,5-triazine; 2-octylmercapto-4,6-bis(3,5-di-tert-butyl-4-hydroxyanilino)-1,3,5-triazine; 2-octylmercapto-4,6-bis(3,5-di-tert-butyl-4-hydroxyphenoxy)-1,3,5-triazine; 2,4,6-tris(3,5-di-tert-butyl-4-hydroxyphenoxy)-1,3,5-triazine; 1,3,5-tris(3,5-di-tert-butyl-4-hydroxybenzyl)isocyanurate; 1,3,5-tris(4-tert-butyl-3-hydroxy-2,6-dimethylbenzyl)isocyanurate; 2,4,6-tris(3,5-di-tert-butyl-4-hydroxyphenylethyl)-1,3,5-triazine; 1,3,5-tris(3,5-di-tert-butyl-4-hydroxyphenylpropionyl)-hexahydro-1,3,5-triazine; and 1,3,5-tris(3,5-dicyclohexyl-4-hydroxybenzyl)isocyanurate.

(xi) Benzylphosphonates such as dimethyl-2,5-di-tert-butyl-4-hydroxybenzylphosphonate; diethyl-3,5-di-tert-butyl-4-hydroxybenzylphosphonate; dioctadecyl-3,5-di-tert-butyl-4-hydroxybenzylphosphonate; dioctadecyl-5-tertbutyl-4-hydroxy-3-methylbenzylphosphonate; and the calcium salt of the monoethyl ester of 3,5-di-tert-butyl-4-hydroxybenzylphosphonic acid.

(xii) Acylaminophenols such as 4-hydroxylauranilide; 4-hydroxystearanilide; and octyl N-(3,5-di-tert-butyl-4-hydroxyphenyl)carbamate.

(xiii) Esters of β-(3,5-di-tert-butyl-4-hydroxyphenyl) propionic acid with mono- or polyhydric alcohols such as methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane and 4-hydroxymethyl-1-phospha-2,6,7-trioxabicyclo[2.2.2] octane.

(xiv) Esters of β-(5-tert-butyl-4-hydroxy-3-methylphenyl) propionic acid with mono- or polyhydric alcohols such as methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane and 4-hydroxymethyl-1-phospha-2,6,7-trioxabicyclo[2.2.2] octane.

(xv) Esters of β-(3,5-dicyclohexyl-4-hydroxyphenyl) propionic acid with mono- or polyhydric alcohols such as methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)-oxamide, 3-thiaundecanol, 3-thiapentadecanol, trimethylhexanediol, trimethylolpropane and 4-hydroxymethyl-1-phospha-2,6,7-trioxabicyclo[2.2.2] octane.

(xvi) Esters of 3,5-di-tert-butyl-4-hydroxyphenyl acetic acid with mono- or polyhydric alcohols such as methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

(xvii) Amides of β-(3,5-di-tert-butyl-4-hydroxyphenyl) propionic acid such as N,N'-bis(3,5-di-tert-butyl-4-hydroxyphenylpropionyl)hexamethylenediamine; N,N'-bis(3,5-di-tert-butyl-4-hydroxyphenylpropionyl) trimethylenediamine; and N,N'-bis(3,5-di-tert-butyl-4-hydroxyphenylpropionyl)hydrazine.

(xviii) Ascorbic acid (Vitamin C).

(xix) Aminic antioxidants such as N,N'-diisopropyl-p-phenylenediamine; N,N'-di-sec-butyl-p-phenylenediamine; N,N'-bis(1,4-dimethylpentyl)-p-phenylenediamine; N,N'-bis(1-ethyl-3-methylpentyl)-p-phenylenediamine; N,N'-bis(1-methylheptyl)-p-phenylenediamine; N,N'-dicyclohexyl-p-phenylenediamine; N,N'-diphenyl-p-phenylenediamine; N,N'-bis(2-naphthyl)-p-phenylenediamine; N-isopropyl-N'-phenyl-p-phenylenediamine; N-(1,3-dimethylbutyl)-N'-phenyl-p-phenylenediamine; N-(1-methylheptyl)-N'-phenyl-p-phenylenediamine; N-cyclohexyl-N'-phenyl-p-phenylenediamine; 4-(p-toluenesulfonamoyl) diphenylamine; N,N'-dimethyl-N,N'-di-sec-butyl-p-phenylenediamine; diphenylamine; N-allyldiphenylamine; 4-isopropoxydiphenylamine; N-phenyl-1-naphthylamine; N-(4-tert-octylphenyl)-1-naphthylamine; N-phenyl-2-naphthylamine; octylated diphenylamine such as p,p'-di-tert-octyldiphenylamine; 4-n-butylaminophenol; 4-butyrylaminophenol; 4-nonanoylaminophenol; 4-dodecanoylaminophenol; 4-octadecanoylaminophenol; bis(4-methoxyphenyl) amine; 2,6-di-tert-butyl-4-dimethylaminomethylphenol; 2,4'-diaminophenylmethane; 4,4'-diaminodiphenylmethane; N,N,N',N'-tetramethyl-4,4'-diaminodiphenylmethane; 1,2-bis[(2-methylphenyl) amino]ethane; 1,2-bis(phenylamino)propane; (o-tolyl) biguanide; bis[4-(1',3'-dimethylbutyl)phenyl]amine; tert-octylated N-phenyl-1-naphthylamine; a mixture of mono- and dialkylated tert-butyl/tert-octyldiphenylamines, a mixture of mono- and dialkylated nonyidiphenylamines; a mixture of mono- and dialkylated dodecyldiphenylamines; a mixture of mono- and dialkylated isopropyl/isohexyldiphenylamines, a mixture of mono- and dialkylated tert-butyldiphenylamines; 2,3-dihydro-3,3-dimethyl-4H-1,4-benzothiazine; phenothiazine; a mixture of mono- and dialkylated tert-butyl/tert-octyl phenothiazines; a mixture of mono- and dialkylated tert-octylphenothiazines; N-allylphenothiazine; N,N,N',N'-tetraphenyl-1,4-diaminobut-2-ene; N,N-bis(2,2,6,6-tetramethylpiperid-4-yl)hexamethylenediamine; bis(2,2,6,6-tetramethylpiperid-4-yl)sebacate; 2,2,6,6-tetramethylpiperidin-4-one; and 2,2,6,6-tetramethylpiperidin-4-ol.

b. UV-absorbers and light stabilizers (i) 2-(2'-Hydroxyphenyl)benzotriazoles such as 2-(2'-hydroxy-5'-methylphenyl)-benzotriazole; 2-(3',5'-di-tert-butyl-2'-hydroxyphenyl)benzotriazole; 2-(5'-tert-butyl-2'-hydroxyphenyl)benzotriazole; 2-(2'-hydroxy-5'-(1,1,3,3-tetramethylbutyl)phenyl)benzotriazole; 2-(3',5'-di-tert-butyl-2'-hydroxyphenyl)-5-chlorobenzotriazole; 2-(3'-tert-butyl-2'-hydroxy-5'-methylphenyl)-5-chloro-benzotriazole; 2-(3'-sec-butyl-5'-tert-butyl-2'-hydroxyphenyl)-benzotriazole; 2-(2'-hydroxy-4'-octoxyphenyl)benzotriazole; 2-(3',5'-di-tert-amyl-2'-hydroxphenyl)benzotriazole; 2-(3',5'-bis(α,α-dimethylbenzyl)-2'-hydroxyphenyl)-benzotriazole; a mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole and 2-(3'-tert-butyl-2'-hydroxy-5'-(2-isooctyloxycarbonylethyl)phenylbenzotriazole; 2,2-methylenebis[4-(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl]benzotriazole with polyethylene glycol 300; and [R—CH$_2$CH—COO(CH$_2$)$_3$]$_2$—where R=3'-tert-butyl-4'-hydroxy-5'-2H-benzotriazol-2-ylphenyl.

(ii) 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

(iii) Esters of substituted and unsubstituted benzoic acids such as 4-tert-butyl-phenyl salicylate; phenyl salicylate; octylphenyl salicylate; dibenzoyl resorcinol; bis(4-tert-butylbenzoyl) resorcinol; benzoyl resorcinol; 2,4-di-tert-butylphenyl 3,5-di-tert-butyl-4-hydroxybenzoate; hexadecyl 3,5-di-tert-butyl-4-hydroxybenzoate; octadecyl 3,5-di-tert-butyl-4-hydroxybenzoate; and 2-methyl-4,6-di-tert-butylphenyl 3,5-di-tert-butyl-4-hydroxybenzoate.

(iv) Acrylates such as ethyl α-cyano-β,β-diphenylacrylate; isooctyl α-cyano-β,β-diphenylacrylate; methyl α-carbomethoxycinnamate; methyl α-cyano-β-methyl-p-methoxycinnamate; butyl α-cyano-β-methyl-p-methoxycinnamate; methyl α-carbomethoxy-p-methoxycinnamate; and N-(β-carbomethoxy-β-cyanovinyl)-2-methylindoline.

(v) Nickel compounds such as nickel complexes of 2,2'-thio-bis-[4-(1,1,3,3-tetramethylbutyl)phenol], including the 1:1 or 1:2 complex, with or without additional ligands such as n-butylamine, triethanolamine or N-cyclohexyldiethanolamine; nickel dibutyldithiocarbamate; nickel salts of monoalkyl esters including the methyl or ethyl ester of 4-hydroxy-3,5-di-tert-butylbenzylphosphonic acid; nickel complexes of ketoximes including 2-hydroxy-4-methylphenyl undecyl ketoxime; and nickel complexes of 1-phenyl-4-lauroyl-5-hydroxypyrazole, with or without additional ligands.

(vi) Sterically hindered amines as well as the N derivatives thereof (e.g., N-alkyl, N-hydroxy, N-alkoxy and N-acyl), such as bis(2,2,6,6-tetramethylpiperidin-4-yl) sebacate; bis(2,2,6,6-tetramethylpiperidin-4-yl)succinate; bis(1,2,2,6,6-pentamethylpiperidin-4-yl)sebacate; bis(1-octyloxy-2,2,6,6-tetramethylpiperidin-4-yl)sebacate; bis(1,2,2,6,6-pentamethylpiperidin-4-yl) n-butyl 3,5-di-tert-butyl-4-hydroxybenzylmalonate; the condensate of 1-(2-hydroxyethyl)-2,2,6,6-tetramethyl-4-hydroxypiperidine and succinic acid; the condensate of N,N'-bis(2,2,6,6-tetramethylpiperidin-4-yl)hexamethylenediamine and 4-tert-octylamino-2,6-dichloro-1,3,5-triazine; tris(2,2,6,6-tetramethylpiperidin-4-yl) nitrilotriacetate; tetrakis(2,2,6,6-tetramethylpiperidin-4-yl)-1,2,3,4-butanetetracarboxylate; 1,1'-(1,2-ethanediyl)bis(3,3,5,5-tetramethylpiperazinone); 4-benzoyl-2,2,6,6-tetramethylpiperidine; 4-stearyloxy-2,2,6,6-tetramethylpiperidine; bis(1,2,2,6,6-pentamethylpiperidyl)-2-n-butyl-2-(2-hydroxy-3,5-di-tert-butylbenzyl)malonate; 3-n-octyl-7,7,9,9-tetramethyl-1,3,8-triazaspiro[4.5]decan-2,4-dione; bis(1-octyloxy-2,2,6,6-tetramethylpiperidyl)sebacate; bis(1-octyloxy-2,2,6,6-tetramethylpiperidyl)succinate; the condensate of N,N'-bis(2,2,6,6-tetramethylpiperidin-4-yl) hexamethylenediamine and 4-morpholino-2,6-dichloro-1,3,5-triazine; the condensate of 2-chloro-4,6-bis(4-n-butylamino-2,2,6,6-tetramethylpiperidyl)-1,3,5-triazine and 1,2-bis(3-aminopropylamino)ethane; the condensate of 2-chloro-4,6-bis(4-n-butylamino-1,2,2,6,6-pentamethylpiperidyl)-1,3,5-triazine and 1,2-bis-(3-aminopropylamino)ethane; 8-acetyl-3-dodecyl-7,7,9,9-tetramethyl-1,3,8-triazaspiro[4.5]decane-2,4-dione; 3-dodecyl-1-(2,2,6,6-tetramethylpiperidin-4-yl) pyrrolidin-2,5-dione; 3-dodecyl-1-(1-ethanoyl-2,2,6,6-tetramethylpiperidin-4-yl)pyrrolidin-2,5-dione; 3-dodecyl-1-(1,2,2,6,6-pentamethylpiperidin-4-yl) pyrrolidine-2,5-dione; a mixture of 4-hexadecyloxy- and 4-stearyloxy-2,2,6,6-tetramethylpiperidine; the condensate of N,N'-bis(2,2,6,6-tetramethylpiperidin-4-yl) hexamethylenediamine and 4-cyclohexylamino-2,6-dichloro-1,3,5-triazine; the condensate of 1,2-bis(3-aminopropylamino)ethane, 2,4,6-trichloro-1,3,5-triazine and 4-butylamino-2,2,6,6-tetramethylpiperidine (CAS Reg. No. [136504-96-6]); 2-undecyl-7,7,9,9-tetramethyl-1-oxa-3,8-diaza-4-oxospiro[4.5]decane; oxo-piperanzinyl-triazines or so-called PIP-T HALS, e.g., GOODRITE® 3034, 3150 and 3159 and similar materials disclosed in U.S. Pat. No. 5,071,981; photobondable HALS such as SANDUVOR® PR-31 and PR-32 (Clariant Corp.) and similar materials disclosed in GB-A-2269819; and the reaction product of 7,7,9,9-tetramethyl-2-cycloundecyl-1-oxa-3,8-diaza-4-oxospiro[4.5]decane and epichlorohydrin. See also generally U.S. Pat. No. 4,619,956, U.S. Pat. No. 5,106,891, GB-A-2269819, EP-A-0309400, EP-A-0309401, EP-A-0309402 and EP-A-0434608, which (to the extent not already done so) are incorporated herein by reference as if fully set forth.

(vii) Oxamides such as 4,4'-dioctyloxyoxanilide; 2,2'-diethoxyoxanilide; 2,2'-dioctyloxy-5,5'-di-tert-butoxanilide; 2,2'-didodecyloxy-5,5'-di-tert-butyloxanilide; 2-ethoxy-2'-ethyloxanilide; N,N'-bis(3-dimethylaminopropyl)oxamide; 2-ethoxy-5-tert-butyl-2'-ethyloxanilide and its mixture with 2-ethoxy-2'-ethyl-5,4'-di-tert-butoxanilide; and mixtures of o- and p-methoxy disubstituted oxanilides and mixtures of o- and p-ethoxy disubstituted oxanilides.

(viii) 2-(2-Hydroxyphenyl)-1,3,5-triazines disclosed in the previously incorporated references, such as 2,4,6-tris(2-hydroxy-4-octyloxyphenyl)-1,3,5-triazine; 2-(2-hydroxy-4-n-octyloxyphenyl)-4,6-bis(2,4-dimethylphenyl)-1,3,5-triazine; 2-(2-hydroxy-4-(mixed iso-octyloxyphenyl)-4,6-bis(2,4-dimethylphenyl)-1,3,5-triazine; 2-(2,4-dihydroxyphenyl)-4,6-bis(2,4-dimethylphenyl)-1,3,5-triazine; 2,4-bis(2-hydroxy-4-propyloxyphenyl)-6-(2,4-dimethylphenyl)-1,3,5-triazine; 2-(2-hydroxy-4-octyloxyphenyl)-4,6-bis(4-methylphenyl)-1,3,5-triazine; 2-(2-hydroxy-4-dodecyloxyphenyl)-4,6-bis(2,4-dimethylphenyl)-1,3,5-triazine; 2-(2-hydroxy-4-tridecyloxyphenyl)-4,6-bis(2,4-dimethylphenyl)-1,3,5-triazine; 2-[2-hydroxy-4-(2-hydroxy-3-butyloxypropyloxy)phenyl]-4,6-bis(2,4-dimethylphenyl)-1,3,5-triazine; 2-[2-hydroxy-4-(2-hydroxy-3-octyloxypropyloxy)-phenyl]-4,6-bis(2,4-dimethylphenyl)-1,3,5-triazine; 2-[4-dodecyloxy/tridecyloxy-2-hydroxypropoxy)-2-hydroxyphenyl]-4,6-bis(2,4-dimethylphenyl)-1,3,5-triazine; 2-[2-hydroxy-4-(2-hydroxy-3-dodecyloxypropoxy)phenyl]-4,6-bis (2,4-dimethylphenyl)-1,3,5-triazine; 2-(2-hydroxy-4-hexyloxy) phenyl-4,6-diphenyl-1,3,5-triazine; 2-(2-hydroxy-4-methoxyphenyl)-4,6-diphenyl-1,3,5-triazine; 2,4,6-tris[2-hydroxy-4-(3-butoxy-2-hydroxypropoxy) phenyl]-1,3,5-triazine; and 2-(2-hydroxyphenyl)-4-(4-methoxyphenyl)-6-phenyl-1,3,5-triazine.

(c) Metal deactivators such as N,N'-diphenyloxamide; N-salicylal-N'-salicyloyl hydrazine; N,N'-bis(salicyloyl) hydrazine; N,N'-bis(3,5-di-tert-butyl-4-hydroxyphenylpropionyl) hydrazine; 3-salicyloylamino-1,2,4-triazole; bis(benzylidene)oxalyl dihydrazide; oxanilide; isophthaloyl dihydrazide; sebacoyl bisphenylhydrazide; N,N'-diacetyladipoyl dihydrazide; N,N'-bis(salicyloyl) oxalyl dihydrazide; and N,N'-bis(salicyloyl)thiopropionyl dihydrazide.

(d) Phosphites and phosphonites, such as triphenyl phosphite; diphenyl alkyl phosphites; phenyl dialkyl phosphites; tris(nonylphenyl) phosphite; trilauryl phosphite; trioctadecyl phosphite; distearyl pentaerythritol diphosphite; tris(2, 4-di-tert-butylphenyl)phosphite; diisodecyl pentaerythritol diphosphite; bis(2,4,-di-tert-butylphenyl)pentaerythritol diphosphite; bis(2,6-di-tert-butyl-4-methylphenyl) pentaerythritol diphosphite; bis(isodecyloxy)pentaerythritol diphosphite; bis(2,4-di-tert-butyl-6-methylphenyl) pentaerythritol diphosphite; bis(2,4,6-tris(tert-butyl)phenyl) pentaerythritol diphosphite; tristearyl sorbitol triphosphite; tetrakis(2,4-di-tert-butylphenyl)-4,4'-biphenylene diphosphonite; 6-isooctyloxy-2,4,8,10-tetra-tert-butyl-12H-dibenzo[d,g]-1,3,2-dioxaphosphocin; 6-fluoro-2,4,8,10-tetra-tert-butyl-12-methyl-dibenzo[d,g]-1,3,2-dioxaphosphocin; bis(2,4-di-tert-butyl-6-methylphenyl) methylphosphite; and bis(2,4-di-tert-butyl-6-methylphenyl) ethylphosphite.

(e) Hydroxylamines such as N,N-dibenzylhydroxylamine; N,N-diethylhydroxylamine; N,N-dioctylhydroxylamine; N,N-dilaurylhydroxylamine; N,N-ditetradecylhydroxylamine; N,N-dihexadecylhydroxylamine; N,N-dioctadecylhydroxylamine; N-hexadecyl-N-octadecyl-hydroxylamine; N-heptadecyl-N-octadecylhydroxylamine; and N,N-dialkylhydroxylamine derived from hydrogenated tallow fatty amines.

(f) Nitrones such as N-benzyl-alpha-phenyl nitrone; N-ethyl-alpha-methyl nitrone; N-octyl-alpha-heptyl nitrone; N-lauryl-alpha-undecyl nitrone; N-tetradecyl-alpha-tridecyl nitrone; N-hexadecyl-alpha-pentadecyl nitrone; N-octadecyl-alpha-heptadecyl nitrone; N-hexadecyl-alpha-heptadecyl nitrone; N-octadecyl-alpha-pentadecyl nitrone; N-heptadecyl-alpha-heptadecyl nitrone; N-octadecyl-alpha-hexadecyl nitrone; and nitrones derived from N,N-dialkylhydroxylamines prepared from hydrogenated tallow fatty amines.

(g) Thiosynergists such as dilauryl thiodipropionate and distearyl thiodipropionate.

(h) Peroxide scavengers such as esters of β-thiodipropionic acid, for example the lauryl, stearyl, myristyl or tridecyl esters; mercaptobenzimidazole or the zinc salt of 2-mercaptobenzimidazole; zinc dibutyidithiocarbamate; dioctadecyl disulfide; and pentaerythritol tetrakis(β-dodecylmercapto)propionate.

(i) Polyamide stabilizers such as copper salts in combination with iodides and/or phosphorus compounds and salts of divalent manganese.

(j) Basic co-stabilizers such as melamine; polyvinylpyrrolidone; dicyandiamide; triallyl cyanurate; urea derivatives; hydrazine derivatives; amines; polyamides; polyurethanes; alkali metal salts and alkaline earth metal salts of higher fatty acids, for example calcium stearate, zinc stearate, magnesium behenate, magnesium stearate, sodium ricinoleate and potassium palmitate; antimony pyrocatecholate; and tin pyrocatecholate.

(k) Nucleating agents including inorganic substances such as talc and metal oxides (e.g. titanium oxide or magnesium oxide) and phosphates, carbonates and sulfates of, preferably, alkaline earth metals; organic compounds such as mono- or polycarboxylic acids and salts thereof, for example 4-tert-butylbenzoic acid, adipic acid, diphenylacetic acid, sodium succinate and sodium benzoate; and polymeric compounds such as ionic copolymers ("ionomers").

(l) Fillers and reinforcing agents such as calcium carbonate; silicates; glass fibers; asbestos; talc; kaolin; mica; barium sulfate; metal oxides and hydroxides; carbon black; graphite; wood flour and flours or fibers from other natural products; and synthetic fibers.

(m) Other additives such as plasticizers, lubricants, emulsifiers, pigments, rheological additives, catalysts, levelling assistants, optical brighteners, flameproofing agents, antistatic agents and blowing agents.

(n) Benzofuranones and indolinones such as those disclosed in U.S. Pat. No. 4,325,863, U.S. Pat. No. 4,338,244, U.S. Pat. No. 5,175,312, U.S. Pat. No. 5,216,052, U.S. Pat. No. 5,252,643, DE-A-4316611, DE-A-4316622, DE-A-4316876, EP-A-0589839 and EP-A-0591102; 3-[4-(2-acetoxy-ethoxy)phenyl]-5,7-di-tert-butyl-benzofuran-2-one; 5,7-di-tert-butyl-3-[4-(2-stearoyloxyethoxy)-phenyl] benzofuran-2-one;3,3'-bis[5,7-di-tert-butyl-3-(4-[2-hydroxyethoxy]phenyl)benzofuran-2-one]; 5,7-di-tert-butyl-3-(4-ethoxyphenyl)benzofuran-2-one; 3-(4-acetoxy-3,5-dimethylphenyl)-5,7-di-tert-butyl-benzofuran-2-one; 3-(3,5-dimethyl-4-pivaloyloxyphenyl)-5,7-di-tert-butyl-benzofuran-2-one; and 5,7-di-tert-butyl-3-(3,4-dimethylphenyl)-3H-benzofuran-2-one.

As indicated above, the polyamino-1,3,5-triazines of the present invention may be incorporated into a substrate, e.g., an organic material to be light stabilized, by any of the known techniques for compounding additives. For example, the polyamino-1,3,5-triazines and optionally an additive may be compounded by dry blending with the substrate in powder or granular form, followed by milling, Banbury mixing, molding, casting, extruding, swelling and the like. Alternatively, the polyamino-1,3,5-triazines may be added, as a solution or a slurry in a suitable inert solvent, or dispersant, to the substrate in powder or granular form, the whole mixed intimately in a mixer, and the solvent subsequently removed. As a further possibility, the polyamino-1,3,5-triazines may be added to the substrate during the preparation of the latter, for instance at the latex stage of polymer production, to provide prestabilized polymer material.

The polyamino-1,3,5-triazines of the present invention are suitable for the photochemical stabilization of substrates such as undyed, dyed or printed fiber materials comprising for example, silk, leather, wool, polyamide or polyurethanes, and especially cellulose-containing fiber materials of all kinds. Examples of such fiber materials are the natural cellulose fibers, such as cotton, linen, jute and hemp, and also viscose staple fiber and regenerated cellulose. Preferred textile fiber materials are those of cotton. The polyamino-1,3,5-triazines are also suitable for the photochemical stabilization of hydroxyl-containing fibers in blend fabrics, for example blends of cotton with polyester fibers or polyamide fibers.

To this end, the polyamino-1,3,5-triazine is applied to the textile fiber material by one of the customary dyeing methods, advantageously in a quantity of about 0.01 to about 5% by weight, preferably about 0.1 to about 3% by weight and, in particular, from about 0.25 to about 2% by weight, based on the weight of the fiber material.

The polyamino-1,3,5-triazines can be applied to the fiber material in various ways and fixed on the fiber, especially in the form of aqueous dispersions or printing pastes. The textile fiber materials finished with the polyamino-1,3,5-triazines possess improved protection against photochemical breakdown of the fiber and yellowing phenomena, and, in the case of dyed fibre material, are of enhanced (hot) light fastness.

Processing Advantages

The polyamino-1,3,5-triazines of the present invention have improved, i.e., lower, processing temperatures and accordingly, lower viscosities, than known cyclohexylamino end-capped polyamino-1,3,5-triazine light stabilizers, such as those disclosed in previously incorporated EP-A-0357223. As a result, the polyamino-1,3,5-triazines of formula (I) have the added advantage in that their processing, in particular, their coextrusion or admixture with polymer substrates sought to be light stabilized, requires less heat than for the processing of known cyclohexylamino end-capped polyamino-1,3,5-triazine light stabilizers, which results in minimized thermal degradation of the substrate, as well as an increase in the lifetime of processing equipment and an overall savings in energy and manufacturing costs.

The present invention will be illustrated by reference to the following examples, which are by way of exemplification and not limitation.

EXAMPLE 1

Preparation of a Morpholino End-Capped Polyamino-1,3,5-Triazine

To a 0° C. mixture of 18.54 g (101 mmol) of cyanuric chloride in 52 mL of toluene and 24 mL of water was added 9.97 g (101 mmol) of cyclohexylamine, at a rate such that the temperature of the resulting mixture was maintained at 0 to 10° C. To the resulting mixture was added 8.30 g (104 mmol) of a 50% aqueous solution of NaOH, at a rate such that the temperature of the resulting mixture was maintained at 0 to 10° C. The resulting mixture was then added to a mixture of 35.46 g (90 mmol) of N,N'-bis(2,2,6,6-tetramethyl-4-piperidinyl)-1,6-hexanediamine, 10.53 g (99 mmol) of sodium carbonate and 20 mL of water at 75° C., and heated so as to remove, via distillation, water and toluene as a water/toluene azeotrope until a temperature of 98–102° C. was achieved. Following removal of the azeotrope, the reaction mixture was heated at reflux for a total of 13 hours from the addition of the triazine mixture to the diamine mixture. After this reflux period, 6.83 g (78 mmol) of morpholine and 25 mL of toluene were added, and the resulting mixture was heated at reflux for 1 h. Then, 3.24 g (40.6 mmol) of a 50% aqueous solution of NaOH, followed by 50 mL of toluene, were added, and the resulting mixture was allowed to heat at reflux for an additional hour. After cooling to room temperature, the lower, aqueous phase was removed, and the upper, organic phase was filtered and concentrated in vacuo to afford a morpholino end-capped polyamino-1,3,5-triazine product in accordance with the present invention.

The resulting product was found, by HPSEC, to possess an $M_n$ of 2070 and an $M_w$ of 3630.

EXAMPLE 2

Viscosity Comparison

I. Preparation of Morpholino End-Capped Polyamino-1,3, 5-Triazine

Step 1. To a 250 mL 3-neck round bottom flask, equipped with an overhead stirrer, condenser and thermometer, were charged 26 mL of water and 46 mL of toluene, which was cooled to less than 3° C. using an ice/water bath. 20 g of cyanuric chloride (0.109 moles) was then charged into the flask all at once. 10.8 g of cyclohexylamine (0.109 moles) was then slowly added to the flask at a rate so as to keep the temperature below 10° C., followed by 8.95 g of a 50 wt % aqueous sodium hydroxide solution (0.112 moles) which was also slowly added as a rate so as to keep the temperature below 10° C. The resulting mixture was stirred for 15 minutes at a temperature between 1° and 3° C.

Step 2. While the above reaction was in progress, a 500 mL 3-neck round-bottomed flask, equipped with an overhead stirrer, fraction-cutting distillation head and thermocouple, was charged with 38.3 g of N,N'-bis(2,2,6,6-tetramethyl-4-piperidinyl)-1,6-hexanediamine (0.097 moles), 11.4 g of sodium carbonate (0.108 moles) and 22 mL of water. This mixture was heated to 70° C. and the reaction mixture from Step 1 was charged to this flask all at once. The mixture was heated to reflux while distilling off the toluene/water azeotrope until a temperature of 101° C. was achieved. At this point, 9.5 mL of water and 44 mL of toluene had been distilled off, and the distilling head was switched to total reflux. Reflux was continued for a total time of 13 hours from the addition of the reaction mixture from Step 1. 100 mL of toluene was then added, producing a milky-white mixture, which was cooled to less than 80° C. and split into two equal 105 mL portions.

Step 3. One of these portions was heated was heated to 97–100° C., and 3.7 g of morpholine (0.043 moles) and 13.4 mL of toluene were added. Stirring was continued for one hour at 95–100° C. 1.75 g of a 50 wt % aqueous sodium hydroxide solution, 27 mL of toluene and 3 mL of water were then added, and the heating and stirring continued for an additional 1 hour. The temperature was then brought to 80° C. and the mixture allowed to settle for 30 minutes, after which the aqueous phase was split off. The remaining organic portion was dried azeotropically using a Dean-Stark trap. 2.0 g of celite filter aid was added and the product filtered and stripped of toluene to yield 31 g of a clear amber solid. Analysis of this product yielded the following results:

NMR (CDCl$_3$, 300 MHZ): δ0.81 t, J=12 Hz, 0.5H; (δ1.10s; δ1.13 br s, 9H combined); δ1.18s, 1.6H; δ1.27 br s, 11H; δ1.4–1.77 br m, 6.7H; δ1.9–2.1 br m, 1.5H; δ1.83 dd, J=3, 12 Hz, 0.5H; δ2.63 t, J=7.5 Hz, 0.3H; δ2.87 t br t, J=11.5 Hz, 0.2H; δ3.26 br m, 2H; (δ3.67 br s; δ3.74 br m, 3.2H combined); δ4.44 br m, 0.3H; δ4.58 d, J=7.5 Hz, 0.4H; δ5.0–5.4 br m, 1.0H.

HPSEC $M_n$ 2070

$M_w$ 3630.

II. Preparation of First Cyclohexylamino End-Capped Polyamino-1,3,5-Triazine

Step 3 above was repeated for the second 105 mL portion except that the morpholine was replaced with 4.24 g of cyclohexylamine (0.043 moles). Filtration and solvent strip yielded 21 g of a clear amber solid. Analysis by HPSEC surprisingly revealed an $M_n$ of 2850, indicating a significantly different molecular weight profile, rendering the product unsuitable for a comparative viscosity testing against the above morpholino end-capped product.

III. Preparation of Second Cyclohexylamino End-Capped Polyamino-1,3,5-Triazine

In order to prepare a cyclohexylamino end-capped product of a similar molecular weight profile for comparison purposes, Steps 1 and 2 above were repeated in their entirety except that an aliquot of the product of Step 2 was taken after 10 hours of reaction (as opposed to 13 hours of reaction).

This product was reacted with cyclohexylamine by the procedure as set forth above, resulting in a product possessing an $M_n$ of 2100 and an $M_w$ 3590 (as determined by HPSEC).

IV. Viscosity Comparison

Both the morpholino end-capped and the second cyclohexylamino end-capped products were measured for complex viscosity with the aid of a RMS 605 mechanical spectrometer (Rheometric Scientific Inc.) in the dynamic mode. The test parameters were as follows:

Parallel plates: 25.0 mm or 50.0 mm depending on viscosity

Strain: sinusoidal with angular frequency of 10 radians/s

Gap: 1–2 mm

Temperature ramp: 5° C./min.

Time/measure: 30 s
Atmosphere: nitrogen.

The strains were adjusted to keep torques between 2–20 g/cm.

Sample preparation: The samples, in the form of fine granules, were placed on the lower plate of the rheometer and the temperature raised to form a bubble-free melt. Contact was then made with the upper plate and the sample temperature was allowed to drop until a stiff viscous liquid was attained. Time was allowed for temperature equilibrium, then the gap was set and measurements started.

The results are presented in the table below. As can be seen, the morpholino end-capped product in accordance with the present invention possessed a significant and surprisingly lower viscosity than the comparative cyclohexylamino end-capped product.

|  | Complex Viscosity (Pa.s) | |
| --- | --- | --- |
|  | 200° C. | 210° C. |
| Morpholino End-Capped | 14.38 | 5.92 |
| Second Cyclohexyamino End-Capped Product | 1,833 | 577 |

Although the present invention is described with reference to certain preferred embodiments, it is apparent that modifications and variations thereof may be made by those skilled in the art without departing from the scope of this invention as defined by the appended claims.

A number of references have been cited herein, the entire disclosures of which are incorporated by reference.

What is claimed is:

1. A compound of the general formula (I):

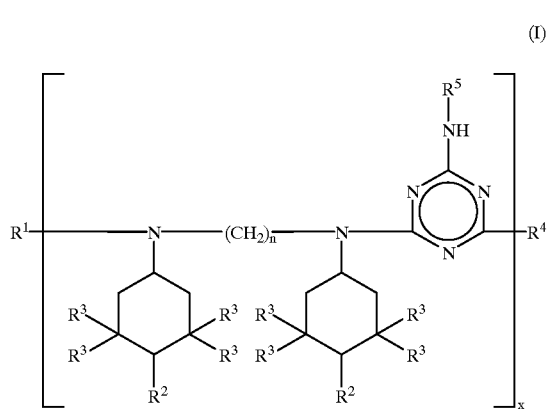

(I)

wherein $R^1$ is selected from hydrogen, hydrocarbyl, hydrocarboyl and a group of the formula (II)

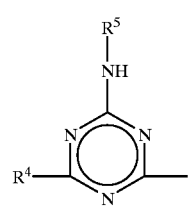

(II)

each $R^2$ is independently selected from hydrogen, oxyl, hydroxy, hydrocarbyl and hydrocarbyloxy;
each $R^3$ is independently selected from an alkyl of 1 to 5 carbon atoms;
each $R^4$ is a morpholino group and each $R^5$ is a cyclohexyl group;
n is 2–12; and
x is 1–50.

2. The compound of claim 1, wherein $R^1$ is selected from hydrogen and a group of the formula (II).

3. The compound of claim 1, wherein $R^2$ is selected from hydrogen, an alkyl of 1 to 4 carbon atoms, an alkoxy of 1 to 4 carbon atoms and an acetyl group.

4. The compound of claim 1, wherein each $R^3$ is methyl.

5. The compound of claim 1, wherein n is 4–8.

6. The compound of claim 1, wherein x is 1–20.

7. The compound of claim 1, wherein $R^1$ is selected from hydrogen and a group of the formula (II); $R^2$ is selected from hydrogen, and alkyl of 1 to 4 carbon atoms, an alkoxy of 1 to 8 carbon atoms and an acetyl group; each $R^3$ is methyl; n is 4–8; and x is 1–20.

8. The compound of claim 1, wherein $R^1$ is selected from hydrogen and a group of the formula (II); $R^2$ is selected from hydrogen, an alkyl of 1 to 4 carbon atoms, an alkoxy of 1 to 4 carbon atoms and an acetyl group; each $R^3$ is methyl; n is 4–8; and x is 1–20.

9. The compound of claim 7, wherein n is 6 and x is 1–15.

10. A stabilizer composition comprising a mixture of compounds of the general formula (I):

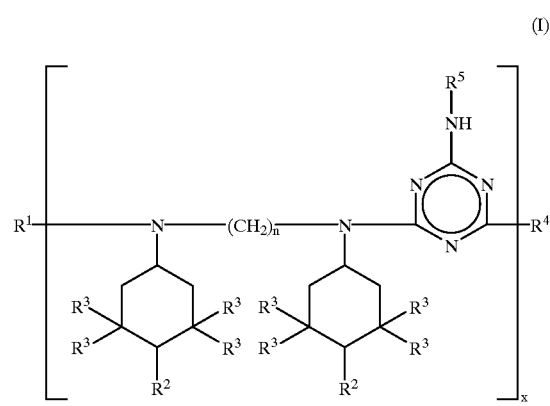

(I)

wherein $R^1$ is selected from hydrogen, hydrocarbyl, hydrocarbyloxy and a group of the formula (II)

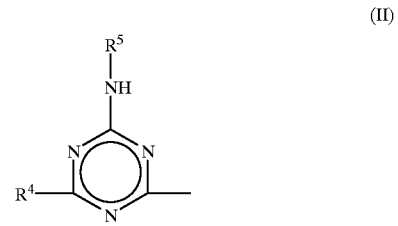

(II)

each $R^2$ is independently selected from hydrogen, oxyl, hydroxy, hydrocarbyl and hydrocarbyloxy;
each $R^3$ is independently selected from an alkyl of 1 to 5 carbon atoms;
each $R^4$ is a morpholino group and each $R^5$ is a cyclohexyl group;
n is 2–12; and
x is 1–50,
said mixture possessing an $M_n$ of from about 1200 to about 3000, and an $M_w$ of from about 2000 to about 5500.

11. The stabilizer composition of claim 9, wherein in the general formula (I): $R^1$ is selected from hydrogen and a group of the formula (II); $R^2$ is selected from hydrogen, an alkyl of 1 to 4 carbon atoms, an alkoxy of 1 to 8 carbon atoms and an acetyl group; each $R^3$ methyl; n is 4–8; and x is 1–20.

12. The stabilizer composition of claim 9, wherein in the general formula (I): $R^1$ is selected from hydrogen and a group of the formula (II); $R^2$ is selected from hydrogen, an alkyl of 1 to 4 carbon atoms, an alkoxy of 1 to 4 carbon atoms and an acetyl group; each $R^3$ is methyl; n is 4–8; and x is 1–20.

13. The stabilizer composition of claim 10, wherein n is 6 and x is 1–15.

14. The stabilizer composition of claim 9, possessing an $M_n$ of from about 1500 to about 2500, and an $M_w$ of from about 2400 to about 4500.

15. The stabilizer composition of claim 9, further comprising another stabilizing additive.

16. The stabilizer composition of claim 10, wherein the another stabilizing additive is selected from an antioxidant, an ultraviolet light absorber, another sterically hindered amine, a phosphite, a thiosynergist and mixtures thereof.

17. A method of stabilizing an organic material against degradation comprising the step of incorporating into the organic material a stabilizingly effective amount of a stabilizer composition as set forth in claim 9.

18. A process for preparing a composition comprising a mixture of compounds of the general formula (I):

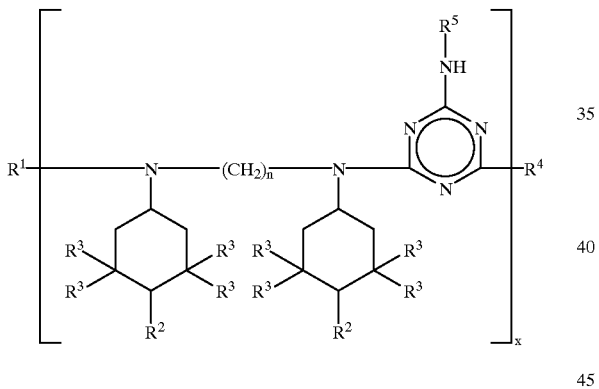

wherein $R^1$ is selected from hydrogen, hydrocarbyl, hydrocarbyloxy and a group of the formula (II)

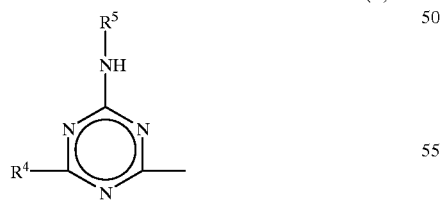

each $R^2$ is independently selected from hydrogen, oxyl, hydroxy, hydrocarbyl and hydrocarbyloxy;

each $R^3$ is independently selected from an alkyl of 1 to 5 carbon atoms;

$R^4$ is a morpholino group;

$R^5$ is a cyclohexylamino group;

n is 2–12;

x is 1–50; and said mixture possessing an $M_n$ of from about 1200 to about 3000, and an $M_w$ of from about 2000 to about 5500, comprising the steps of:

(a) reacting a 2,4,6-trihalocyanurate with cyclohexylamine to afford a 2,6-dihalo-4-cyclohexylamino-1,3,5-triazine intermediate of the formula

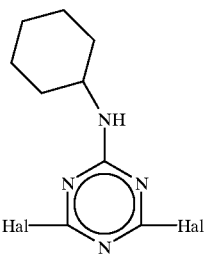

wherein Hal is a halogen;

(b) reacting the 2,6-dihalo-4-cyclohexylamino-1,3,5-triazine intermediate with an N,N-bis(2,2,6,6-tetramethyl-4-piperidinyl)-α,ω-($C_2$–$C_{12}$) alkylenediamine of the formula

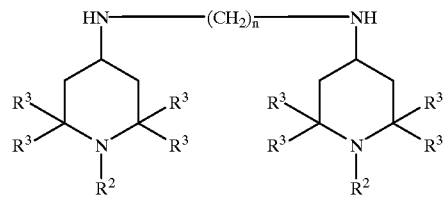

wherein $R^2$, $R^3$ and n are as defined above, to provide a polyamino-1,3,5-triazine intermediate comprising a mixture of compounds of the formula (I), wherein $R^1$, $R^2$, $R^3$, $R^5$, x and n are as defined above, and $R^4$ is Hal; and (c) treating the polyamino-1,3,5-triazine intermediate from step (b) with morpholine to provide the composition.

* * * * *

UNITED STATES PATENT AND TRADEMARK OFFICE
CERTIFICATE OF CORRECTION

PATENT NO. : 6,096,886
DATED : August 1, 2000
INVENTOR(S) : Martin L. Cohen

It is certified that error appears in the above-identified patent and that said Letters Patent is hereby corrected as shown below:

Errors appeared in the aboved-identified patent. The errors are not the fault of the Applicant.

In the Structure, Formula (I),

Column 2,
Lines 1 to 17;

Column 21,
Lines 34 to 48;

Column 22,
Lines 26 to 41;

UNITED STATES PATENT AND TRADEMARK OFFICE
CERTIFICATE OF CORRECTION

PATENT NO. : 6,096,886
DATED : August 1, 2000
INVENTOR(S) : Martin L. Cohen

Page 2 of 2

It is certified that error appears in the above-identified patent and that said Letters Patent is hereby corrected as shown below:

Column 23,
Lines 29 to 43 should appear as follows:

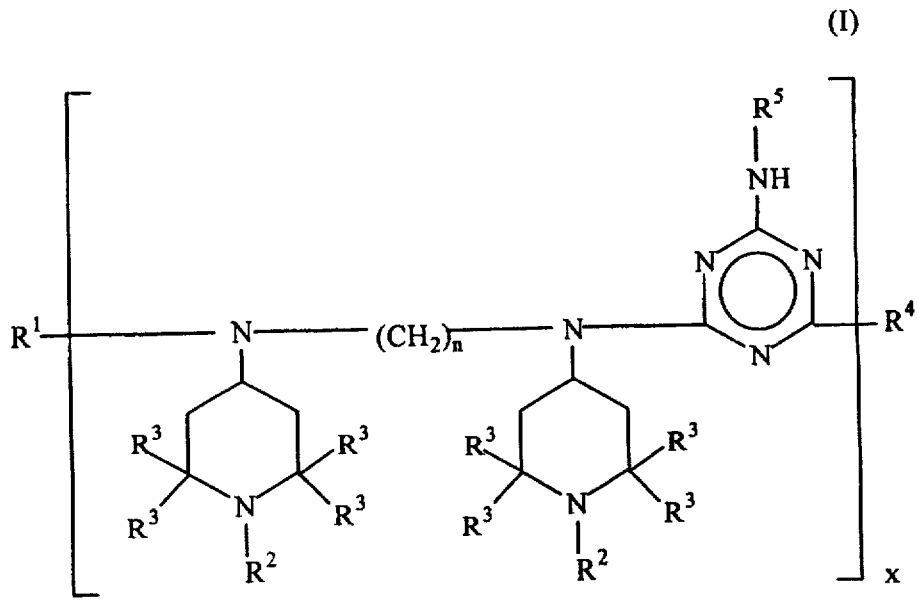

Signed and Sealed this

Twenty-first Day of August, 2001

Attest:

Attesting Officer

NICHOLAS P. GODICI
Acting Director of the United States Patent and Trademark Office